United States Patent [19]

Vic et al.

[11] Patent Number: 5,763,722

[45] Date of Patent: Jun. 9, 1998

[54] METHOD FOR THE METHANE CHEMICAL CONVERSION INTO $C_2$ HYDROCARBONS

[75] Inventors: Sebastian Vic; Miguel A. Peña; Pilar Terreros; Juan P. Gomez; José L. Garcia-Fierro; Juan M. Jimenez, all of Madrid, Spain

[73] Assignee: Repsol Petroleo S.A., Madrid, Spain

[21] Appl. No.: 479,001

[22] Filed: Jun. 7, 1995

Related U.S. Application Data

[63] Continuation of Ser. No. 989,646, Dec. 11, 1992, abandoned.

[51] Int. Cl.[6] .................. C07C 2/00; C07C 2/82; C07C 2/83
[52] U.S. Cl. .................. 585/500; 585/415; 585/417; 585/418; 585/654; 585/656; 585/658; 585/943
[58] Field of Search .................. 585/500, 415, 585/417, 418, 654, 656, 658, 943

[56] References Cited

U.S. PATENT DOCUMENTS

| | | | |
|---|---|---|---|
| 4,499,324 | 2/1985 | Gaffney | 585/943 |
| 4,523,049 | 6/1985 | Jonas et al. | 585/541 |
| 4,801,762 | 1/1989 | Leyshon | 585/500 |
| 4,822,944 | 4/1989 | Brazdil, Jr. et al. | 585/500 |
| 4,950,836 | 8/1990 | Kimble et al. | 585/943 |
| 4,982,041 | 1/1991 | Campbell | 585/500 |

*Primary Examiner*—Elizabeth D. Wood
*Attorney, Agent, or Firm*—Cushman Darby & Cushman IP Group of Pillsbury Madison & Sutro LLP

[57] ABSTRACT

An improved method for the oxidative conversion of methane into higher hydrocarbons in which methane and oxygen are continuously and simultaneously cofed into a reaction zone under effective oxidative coupling conditions and contacted with a solid catalyst consisting essentially of a catalyst having a composition of empirical formula $Ce_aNa_bCa_{100}O_x$ wherein a is in the range 0.03 to 2.0, b is in the range of 0.7 to 7.0 and oxygen is present in a molar amount sufficient to fulfill the valence requirements of cerium, sodium and calcium.

9 Claims, 2 Drawing Sheets

METHOD FOR THE METHANE CHEMICAL CONVERSION INTO $C_2$ HYDROCARBONS

This is a continuation of Application Ser. No. 07/989,646, filed on Dec. 11, 1992 and now abandoned.

The invention refers to an improved method for the methane chemical conversion into more valuable and heavier hydrocarbons. Also refers to an improved catalyst composition for carrying out said method.

BACKGROUND OF THE INVENTION AND DESCRIPTION OF PRIOR ART

Large quantities of natural gas, which is primarily methane, are found at remote areas throughout the world; often it can be transported from the source to the consumer via pipelines. However, there are many situations where this does not apply. Vast quantities are usually flared in the source from where its transport in gaseous form is impossible. In order to save its value and due to its great abundance and low cost, on a carbon basis, there is a strong economic incentive to turn methane into other value-added products. Accordingly, a great deal of effort has been expended to provide improved chemical methods for the conversion of methane into higher boiling hydrocarbons, i.e. $C_2+$ hydrocarbons.

At the present time, ethylene is produced by dehydrogenation or pyrolisis of ethane and propane, naphta and, in some instances, gasoils. Nearly 75% of the ethylene is produced by steam cracking of ethane and propane separated from natural gas. However, typical natural gas does not contain more than 15% volume of other hydrocarbons different from methane, being ethane the major component. Moreover, the separation of propane and ethane from natural gas is an expensive and complex process, involving compression and expansion, cryogenic techniques and their combinations. Considering these disadvantages, the production of ethylene form the most abundant methane source appears to be highly desirable.

When using methane for such a purpose there is, however, a thermodynamic barrier imposed for the great stability of its molecule as compared to that of long chain hydrocarbons. Although pyrolitic or dehydrogenative methane transformations have been proposed, the reactions must take place at temperatures usually above 1000° C. to provide acceptable yields, thus making the process little attractive.

The oxidative transformation of methane or natural gas into longer C-chain hydrocarbons represents indeed the most promising alternative. After the pioneering work of Keller and Bhasin (Journal of Catalysis 73,9,1982) and the intensive efforts expended in the last years, the methodology of the oxidative conversion reached a certain development degree. Worth of noting is the fact that the original process was conducted in a cyclic manner over a redox oxide catalyst: the oxide is first reduced by methane while yielding $C_2+$ products, then the reduced catalyst is oxidized by oxygen or air in order to restore its initial oxidation degree.

It appears that this mode of operation is highly uneconomic since to time-consuming also the implicit complexity of reactor operation should be added. All these problems have been avoided by feeding the reactor simultaneously with methane and oxygen or air in proportions far from the explosion limits. The advantages of this latter methodology have been immediately recognized and used practically for all research groups as documented from the analysis of the large amount of work published on methane conversion.

Apart from the above general considerations, there is no precise knowledge on both the nature of the catalysts and the manner in which they operate. Valid generalizations on the state of the art which make reference to the general characteristic of the catalysts already exist. For instance, catalysts with a marked basic character or with redox properties are needed if they work in the cofeed or in the cyclic mode of operation, respectively. Other important generalization concerning the catalytic systems used for methane conversion refers to the participation of the oxygen of catalysts only in the first steps of the reaction. On surface oxygen the methane transforms into methyl radicals which then desorb to the gas phase where they undergo complex reaction pathway, in which coupling and dehydrogenation are the principal processes.

There are many documents (patents) describing the process of methane conversion into longer chain hydrocarbons over reducible metal oxides, but that related to catalytic systems based on non-reducible metal oxides are less numerous. Among this latter category, U.S. Pat. No. 4,780,449 discloses a catalyst for the conversion of methane into hydrogen and higher hydrocarbons comprising a non-reducible alkaline earth or lanthanide oxide which may be used alone or with up to 50% by weight of one or more promoter oxides such alkaline, alkaline earth, lanthanide or even redox type. The need to incorporate promoters to the alkaline earth oxides able to inhibit the combustion of methane has been recently recognized in the work by X. D. Peng and P. C. Stair (Journal of Catalysis 128,264,1991). These authors demonstrate that a pure calcium oxide catalyst yields essentially carbon dioxide, but if sodium oxide is added both methane conversion and selectivity to higher hydrocarbons are improved. It has been also recently reported by T. Grzybek and M. Baerns (Journal of Catalysis 129,106,1991) that calcium-sodium and calcium-barium-sodium oxide catalysts become easily carbonated when exposed to ambient or during on-stream in methane conversion, although such carbonates appear to be partially reduced by methane during on-stream at temperatures above 500° C. From this information, it appears that a high performance in the methane conversion can be achieved with calcium oxide catalysts if caution is taken in their preparation.

The state of the art in the field of this invention also points out that a large variety of products are formed during the methane conversion. Carbon oxides and water are easily formed due to their high thermodynamic stability, but other compounds such as hydrogen and higher hydrocarbons grouped under $C_2+$ denomination, including ethane, ethylene, propylene and butenes can be formed. In particular circumstances, oxygenated hydrocarbons like methanol and formaldehyde can also be formed although their proportion is usually very low, much more at higher reaction temperatures. It must be also remarked that at present the efficiency of the methane conversion process is not high enough as to make commercially interesting this process.

Based on all the above information could be inferred that the behavior of a given catalyst in the methane conversion is unforeseeable. In addition, the efficiency of a given catalyst, even considered as specific for that purpose, depends to a great extent on the conditions and the manner to conduct the reaction itself. Finally, there is a limited knowledge to predict what conditions or what manner of operation brings about a higher methane conversion or $C_2+$ selectivity, thus rendering more efficient the process.

SUMMARY OF THE INVENTION

The primary object of this invention is to provide an improved method for converting methane into more valuable and heavier hydrocarbons which meets the aforementioned requirements and solves the aforementioned problems of prior art methods. More particularly, objects of the present invention are to provide a method for converting methane into more valuable $C_2+$ hydrocarbons with a high conversion level of methane which affords high $C_2+$ selectivity and high yield.

It is also an object of the present invention to provide an improved catalyst composition for carrying out the conversion of methane into longer chain hydrocarbons.

According to the invention, methane can be converted into $C_2+$ hydrocarbons by following a method wherein a feed material comprising methane and oxygen is contacted with a solid catalyst comprising calcium, at least one alkaline element, one lanthanide element and oxygen, under oxidative conditions sufficient to convert efficiently methane into higher hydrocarbons.

The preferred alkaline element is sodium and the preferred lanthanide element is cerium.

A catalyst for carrying out the method of the invention has a composition of general formula $A_aB_bCa_{100}O_x$, where "A" is a lanthanide element, preferably cerium; "B" is an alkaline element, preferably sodium; "a" is a number in the range 0–100, preferably between 0.2 and 2.0; "b" is a number in the range 0–20, preferably between 0.7 and 7.0, and "x" is the number of oxygen atoms required to fulfill the valence requirements of the other elements.

DETAILED DESCRIPTION OF THE INVENTION

Figure 1:
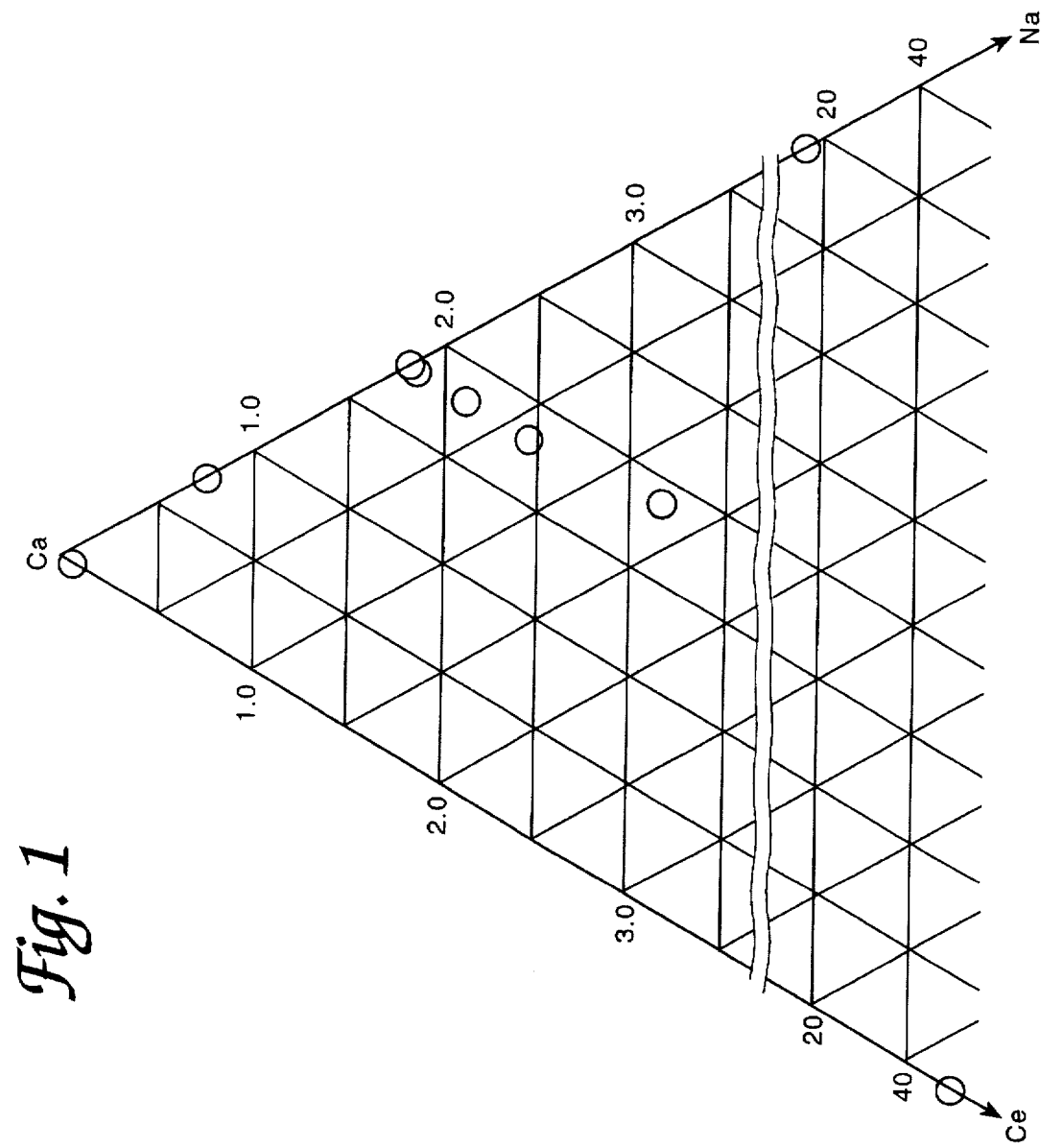
FIG. 1 displays a ternary diagram of catalyst compositions according to the invention.

The catalysts of this invention consist of a compound of general formula $A_aB_bCa_{100}O_x$, where "A" is a lanthanide element, preferably cerium; "B" is an alkaline element, preferably sodium; "a" is a number in the range 0–100, preferably between 0.2 and 2.0; "b" is a number in the range 0–20, preferably between 0.7 and 7.0, and "x" is the number of oxygen atoms required to fulfill the valence requirements of the other elements.

A preferred catalyst according to the invention is an oxide compound of general formula $Ce_aNa_bCa_{100}O_x$ where a=0.33, b=1.84 and "x" is the number of oxygen atoms required to fulfill the valence requirements of cerium, sodium and calcium.

The catalysts according to the invention can be prepared by impregnation, coprecipitation, complexation or by other known methods of the prior art. They are usually prepared by complete solubilization in water of the precursor compounds in a simultaneous manner, but only containing the minoritary elements. The resulting solution is then mixed in a beaker containing the major compound, dried and powdered previously. Then, the impregnate is dried to remove the volatile components followed by calcining in an air atmosphere at temperatures between 600° and 1000° C., but preferably between 700° and 850° C.

Different precursor compounds of the constituting elements of catalyst can also be solubilized by adding a stoichiometric amount of a polyhydroxylated organic complex agent able to complex all metal cations in solution. This solution can then be heated to dryness and subsequently calcined in an air atmosphere at temperatures between 600° and 1000° C., and preferably between 700° and 850° C.

In other alternative method the solubilized solution of the precursor elements can be dropwise added to a $HCO_3^-/H_2CO_3$ buffer solution at 80° C. till complete precipitation of a mixed crystalline carbonate. This carbonate is then dried under vacuum and subsequently calcined in an air atmosphere at temperatures between 600° and 1000° C., and preferably between 700° and 850° C.

These three methods, described above only for illustrative purposes, do not exclude the possibility to use other well known methods of the art. As starting metal precursors several inorganic salts such as nitrates, phosphates, carbonates, silicates, aluminates and halides, or organic salts such as acetates, acethylacetonates, oxalates and formiates, or inorganic oxides and hydroxides, can also be used.

The calcination conditions are selected in order to achieve optimum physical properties of the final catalyst, that is, attrition resistance, specific surface, particle size, etc. The physical shape of the catalyst can accordingly be selected with the conventional techniques of the art, namely tablets, beads or extrudates, or even by supporting the sinterized active catalyst. Oxides such as silica, alumina, zirconia, titania, magnesia and zeolites or active carbon can be selected as possible carriers, although they are not limitative.

Among several catalysts according to the invention prepared to perform the chemical conversion of methane, nine examples have been selected, while FIG. 1 displays a ternary diagram of catalyst compositions, expressed as molar percentage, according to the invention.

EXAMPLE 1

$Na_{0.73}Ca_{100}O_x$ 0.220 g of $NaNO_3$ were solubilized in 200 cm³ of distilled water. The solution was added to 19.92 g of CaO, previously dried at 120° C. The excess of water was then removed in a rotary evaporator at 80° C. till dryness. The resulting impregnate was subsequently heated in an oven at a constant rate of 2° C. per minute until the final temperature of 800° C., and kept at this temperature for 2 h. The calcined product was compacted and sieved to sizes of 0.42–0.59 mm.

EXAMPLE 2

$Na_{1.82}Ca_{100}O_x$ 0.516 g of $NaNO_3$ were solubilized in 200 cm³ of distilled water. The solution was added to 18.63 g of CaO, previously dried at 120° C. The excess of water was then removed in a rotary evaporator at 80° C. till dryness. The resulting impregnate was subsequently heated in an oven at a constant rate of 2° C. per minute until the final temperature of 800° C., and kept at this temperature for 2 h. The calcined product was compacted and sieved to sizes of 0.42–0.59 mm.

EXAMPLE 3

$Na_{20.0}Ca_{100}O_x$ 6.097 g of $NaNo_3$ were solubilized in 200 cm³ of distilled water. The solution was added to 20.01 g of CaO, previously dried at 120° C. The excess of water was then removed in a rotary evaporator at 80° C. till dryness. The resulting impregnate was subsequently heated in an oven at a constant rate of 2° C. per minute until the final temperature of 800° C., and kept at this temperature for 2 h. The calcined product was compacted and sieved to sizes of 0.42–0.59 mm.

EXAMPLE 4

$Ce_{0.03}Ca_{100}O_x$ 0.048 g of $Ce(NO_3)_3 \cdot 6H_2O$ were solubilized in 200 cm³ of distilled water. The solution was added to 18.32 g of CaO, previously dried at 120° C. The excess of water was then removed in a rotary evaporator at 80° C. till dryness. The resulting impregnate was subsequently heated in an oven at a constant rate of 2° C. per minute until the final temperature of 800° C., and kept at this temperature for 2 h. The calcined product was compacted and sieved to sizes of 0.42–0.59 mm.

EXAMPLE 5

$Ce_{0.03}Na_{1.83}Ca_{100}O_x$ 0.053 g of $Ce(NO_3)_3 \cdot 6H_2O$ and 0.562 g of $NaNO_3$ were solubilized in 200 cm³ of distilled water. The solution was added to 20.03 g of CaO, previously dried at 120° C. The excess of water was then removed in a rotary evaporator at 80 ° C. till dryness. The resulting impregnate was subsequently heated in an oven at a constant rate of 2° C. per minute until the final temperature of 800° C., and kept at this temperature for 2 h. The calcined product was compacted and sieved to sizes of 0.42–0.59 mm.

EXAMPLE 6 and EXAMPLE 6a $Ce_{0.33}Na_{1.84}Ca_{100}O_x$ 0.543 g of $Ce(NO_3)_3 \cdot 6H_2O$ and 0.562 g of $NaNO_3$ were solubilized in 200 cm³ of distilled water. The solution was added to 20.12 g of CaO, previously dried at 120° C. The excess of water was then removed in a rotary evaporator at 80° C. till dryness. The resulting impregnate was subsequently heated in an oven at a constant rate of 2° C. per minute until the final temperature of 800° C., and kept at this temperature for 2 h. The calcined product was compacted and sieved to sizes of 0.42–0.59 mm.

EXAMPLE 7

$Ce_{0.67}Na_{1.86}Ca_{100}O_x$ 1.041 g of $Ce(NO_3)_3 \cdot 6H_2O$ and 0.566 g of $NaNO_3$ were solubilized in 200 cm³ of distilled water. The solution was added to 20.01 g of CaO, previously dried at 120° C. The excess of water was then removed in a rotary evaporator at 80° C. till dryness. The resulting impregnate was subsequently heated in an oven at a constant rate of 2° C. per minute until the final temperature of 800° C., and kept at this temperature for 2 h. The calcined product was compacted and sieved to sizes of 0.42–0.59 mm.

EXAMPLE 8

$Ce_{1.37}Na_{1.90}Ca_{100}O_x$ 2.125 g of $Ce(NO_3)_3 \cdot 6H_2O$ and 0.578 g of $NaNO_3$ were solubilized in 200 cm³ of distilled water. The solution was added to 20.01 g of CaO, previously dried at 120° C. The excess of water was then removed in a rotary evaporator at 80° C. till dryness. The resulting impregnate was subsequently heated in an oven at a constant rate of 2° C. per minute until the final temperature of 800° C., and kept at this temperature for 2 h. The calcined product was compacted and sieved to sizes of 0.42–0.59 mm.

EXAMPLE 9

$Ce_{100}Ca_{100}O_x$ 15.223 g of $Ce(NO_3)_3 \cdot 6H2O$ and 8.279 g of $NaNO_3$ were solubilized in 40 cm³ distilled water. The solution was added to other one prepared by solubilizing 13.472 g of citric acid in 40 cm³ of distilled water. The excess of water was then removed at 70° C. until the remainder acquired a high viscosity (viscous syrup). The resulting precursor was then dried at 110° C. for 15 h, followed by heating at a rate of 2° C. per minute until 800° C., then keeping this temperature for 2 h. The calcined product was compacted and sieved to sizes of 0.42–0.59 mm. This material was characterized by its X-ray diffraction pattern, shown in FIG. 2. The arrows in this figure correspond to the silicon peaks because this was used as an internal standard.

According to the invention an enhanced methane conversion, via oxidative coupling, into longer chain hydrocarbons with high selectivities, mainly ethylene and ethane, can be achieved by reaction of a methane and oxygen mixture on a catalyst consisting of calcium, an alkaline element and a lanthanide element, under oxidative conditions, suitable to yield efficiently $C_2+$ hydrocarbons and in the absence of deactivation phenomena during 200 hours on-stream. Water, carbon monoxide and carbon dioxide are major byproducts and the unreacted methane can be recycled in order to increase the efficiency of the process.

According to the invention the preferred alkaline element is sodium and the lanthanide element is cerium.

The catalyst is prepared by combining the precursor ingredients and calcining in air atmosphere. The catalyst is placed in the reaction zone and preheated within the reactor in the reactant gas mixture.

The temperature needed for the oxidative coupling is in the range 500°–1000° C., although it is preferred a narrower range of 650°–800° C. The reactor operates in all cases at pressures near to 1 bar, only a slight excess is introduced as a consequence of the drop pressure through catalyst bed and other flow elements of the system. This peculiarity simplifies to a great extent the control of the reactor since a very simple feed system and reactor control are required. Another important advantage in using such a conditions is to reduce the explosion probability. The residence times of reactants are comprissed between 0.5 and 50 g.h/mol, still when the preferred are between 1 and 30 g.h/mol.

In accordance with the most extended procedure for the oxidative coupling of methane to higher hydrocarbons, particularly ethylene and ethane, the reaction is carried out in a fixed bed flow reactor by cofeeding both methane and oxygen. However, a volumetric ratio methane/oxygen of at least 1, preferably between 1 and 20 is selected. This mode of operation provides a great flexibility for the control of the operation parameters and of the overall process, and simultaneously reduces the extremely long time of operation required by the cyclic feeding.

The method of the invention is suitable for the conversion of methane-rich gas mixtures through the oxidate conversion into ethylene, ethane and higher hydrocarbons ($C_2+$). The gas mixture must be fed simultaneously with other oxygen-rich gas mixture into a fixed bed reactor in order to perform the oxidative conversion over the solid catalyst.

The gas fed is methane, still when a mixture of non interfering gases can be used if the methane content in the feed is comprissed between 25 and 100% molar. Other alternatives to natural gas such as synthetic natural gas (SNG) and products resulting from gasification or carbide materials or from anaerobic digestion of biomass can be also used. The presence of minor amounts of longer chain hydrocarbons (ethane, propane, butane, pentane), water, carbon monoxide, carbon dioxide, nitrogen or inert gases (argon, helium, neon) in the above feeds does not require further purifications.

The oxidant is oxygen, still when a mixture of non interfering gases can be used if the methane content in the feed is comprissed between 21 and 100% molar, preferably above 50% molar. Thus, pure oxygen or diluted mixtures of oxygen and other gases, namely nitrogen, carbon monoxide, carbon dioxide, water or inert gases (argon, helium, neon) can be also used.

To illustrate the process, Table 1 compiles activity data in a given reaction conditions for the aforementioned selected application examples.

TABLE I

| Example | 1 | 1 | 1 | 2 | 2 | 2 |
|---|---|---|---|---|---|---|
| Residence time (g · h/mol) | 20 | 20 | 20 | 20 | 20 | 20 |
| Molar ratio $CH_4/O_2$ | 4 | 4 | 4 | 4 | 4 | 4 |
| Total pressure (bar) | 1 | 1 | 1 | 1 | 1 | 1 |
| Temperature (°C.) | 700 | 750 | 800 | 700 | 750 | 800 |
| Methane conversion % | 13.8 | 29.1 | 29.0 | 13.0 | 29.1 | 28.2 |
| $C_2$+ selectivity % | 54.4 | 61.1 | 61.9 | 51.8 | 60.7 | 61.9 |
| Ethylene yield % | 2.7 | 9.5 | 11.0 | 2.3 | 9.2 | 9.4 |
| Ethane yield % | 4.4 | 6.6 | 5.4 | 4.2 | 6.8 | 6.4 |
| CO yield % | 0.7 | 0.3 | 0.7 | 0.7 | 0.3 | 0.4 |
| $CO_2$ yield % | 5.6 | 11.0 | 10.3 | 5.6 | 11.1 | 10.4 |
| Example | 3 | 3 | 3 | 4 | 4 | 4 |
| Residence time (g · h/mol) | 20 | 20 | 20 | 20 | 20 | 20 |
| Molar ratio $CH_4/O_2$ | 4 | 4 | 4 | 4 | 4 | 4 |
| Total pressure (bar) | 1 | 1 | 1 | 1 | 1 | 1 |
| Temperature (°C.) | 700 | 750 | 800 | 700 | 750 | 800 |
| Methane conversion % | 12.1 | 27.3 | 28.5 | 20.1 | 26.8 | 27.2 |
| $C_2$+ selectivity % | 56.0 | 61.0 | 62.8 | 39.2 | 46.1 | 43.9 |
| Ethylene yield % | 2.5 | 9.3 | 10.5 | 3.3 | 5.9 | 7.1 |
| Ethane yield % | 4.0 | 5.8 | 5.3 | 4.1 | 5.6 | 4.3 |
| CO yield % | 0.5 | 0.7 | 0.1 | 2.3 | 1.9 | 2.9 |
| $CO_2$ yield % | 4.9 | 9.9 | 10.5 | 9.9 | 12.5 | 12.3 |
| Example | 5 | 5 | 5 | 6 | 6 | 6 |
| Residence time (g · h/mol) | 20 | 20 | 20 | 20 | 20 | 20 |
| Molar ratio $CH_4/O_2$ | 4 | 4 | 4 | 4 | 4 | 4 |
| Total pressure (bar) | 1 | 1 | 1 | 1 | 1 | 1 |
| Temperature (°C.) | 700 | 750 | 800 | 700 | 750 | 800 |
| Methane conversion % | 15.7 | 29.7 | 28.8 | 17.7 | 29.7 | 28.3 |
| $C_2$+ selectivity % | 56.4 | 60.1 | 63.4 | 60.7 | 60.2 | 62.6 |
| Ethylene yield % | 3.7 | 9.6 | 10.6 | 4.9 | 9.6 | 10.3 |
| Ethane yield % | 4.7 | 6.5 | 6.0 | 5.2 | 6.5 | 5.8 |
| CO yield % | 0.9 | 0.3 | 0.5 | 0.7 | 0.3 | 0.6 |
| $CO_2$ yield % | 5.9 | 11.6 | 10.1 | 6.3 | 11.5 | 10.0 |
| Example | 7 | 7 | 7 | 8 | 8 | 8 |
| Residence time (g · h/mol) | 20 | 20 | 20 | 20 | 20 | 20 |
| Molar ratio $CH_4/O_2$ | 4 | 4 | 4 | 4 | 4 | 4 |
| Total pressure (bar) | 1 | 1 | 1 | 1 | 1 | 1 |
| Temperature (°C.) | 700 | 750 | 800 | 700 | 750 | 800 |
| Methane conversion % | 18.1 | 29.2 | 28.5 | 19.1 | 29.8 | 28.3 |
| $C_2$+ selectivity % | 55.9 | 60.9 | 60.0 | 56.7 | 59.8 | 60.7 |
| Ethylene yield % | 4.4 | 9.4 | 10.2 | 5.0 | 9.5 | 10.1 |
| Ethane yield % | 5.1 | 6.7 | 5.6 | 0.9 | 0.2 | 0.6 |
| CO yield % | 0.9 | 0.2 | 1.0 | 0.9 | 0.2 | 0.6 |
| $CO_2$ yield % | 7.1 | 11.2 | 10.5 | 7.4 | 11.8 | 10.5 |
| Example | 9 | 9 | 9 | 6a | 6a | 6a |
| Residence time (g · h/mol) | 20 | 20 | 20 | 20 | 20 | 20 |
| Molar ratio $CH_4/O_2$ | 4 | 4 | 4 | 2 | 2 | 2 |
| Total pressure (bar) | 1 | 1 | 1 | 1 | 1 | 1 |
| Temperature (°C.) | 700 | 750 | 800 | 700 | 750 | 800 |

TABLE I-continued

| Methane conversion % | 20.5 | 22.3 | 21.6 | 15.1 | 34.6 | 46.2 |
|---|---|---|---|---|---|---|
| $C_2$+ selectivity % | 31.6 | 39.1 | 30.8 | 43.7 | 43.9 | 43.5 |
| Ethylene yield % | 2.0 | 3.7 | 4.1 | 2.9 | 9.9 | 13.2 |
| Ethane yield % | 4.1 | 4.6 | 2.4 | 3.4 | 4.3 | 4.9 |
| CO yield % | 1.2 | 1.1 | 2.7 | 1.5 | 3.6 | 1.4 |
| $CO_2$ yield % | 12.8 | 12.5 | 12.3 | 7.0 | 15.8 | 24.7 |

We claim:

1. A method for the oxidative coupling of methane to form longer hydrocarbons comprising cofeeding methane and oxygen simultaneously and continuously into a reaction zone to effect contact at a reaction temperature of at least 500° C. under oxidative coupling reaction conditions with a solid catalyst consisting essentially of calcium, sodium, cerium and oxygen, having a composition of empirical formula $Ce_aNa_bCa_{100}O_x$ wherein a is in the range 0.03 to 2.0, b is in the range 0.7 to 7.0 and oxygen is present in a molar amount sufficient to fulfill the valence requirements of cerium, sodium and calcium.

2. A method in accordance with claim 1, wherein the catalyst has been prepared by calcining in an air atmosphere.

3. A method, in accordance with claim 1, further comprising preheating the solid catalyst within the reaction zone.

4. A method, in accordance with claim 1, further comprising maintaining the reaction temperature between 650° and 800° C.

5. A method, in accordance with claim 1, wherein the reaction zone is a fixed bed reactor.

6. A method, in accordance with claim 1, wherein volumetric ration methane/oxygen is at least 1.

7. A method, in accordance with claim 1, further comprising maintaining a volumetric ratio methane/oxygen between 1 and 20.

8. A method, in accordance with claim 1, wherein the solid catalyst has a composition of empirical formula $Ce_{0.33}Na_{1.84}Ca_{100}O_x$ where x is the molar amount of oxygen sufficient to fulfill the valence requirements cerium, sodium and calcium.

9. A method, in accordance with claim 1, wherein the pressure of operation is 1 bar, and the residence time is in the range 10 to 20 gh/mol.

* * * * *

UNITED STATES PATENT AND TRADEMARK OFFICE
CERTIFICATE OF CORRECTION

PATENT NO. : 5,763,722

DATED : June 9, 1998

INVENTOR(S) : Vic, et al

Figure 2A:
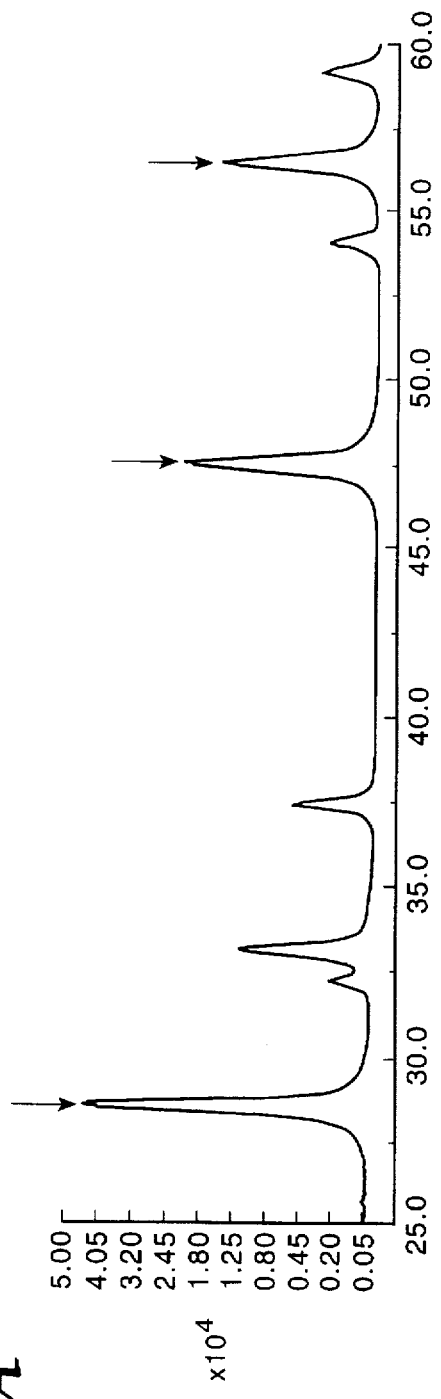
FIG. 2 shows X-ray diffraction pattern of a particular example of catalyst.
Figure 2B:
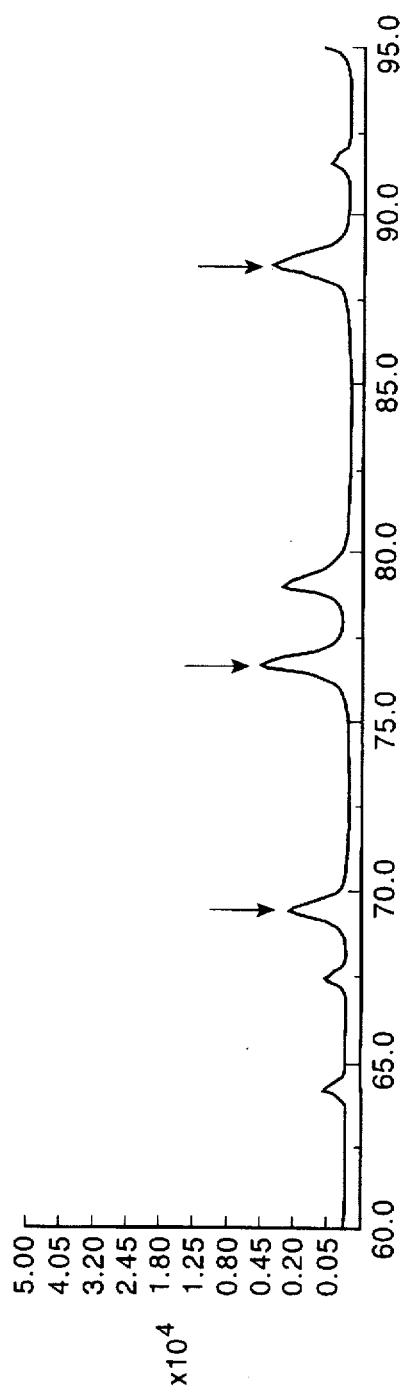

It is certified that error appears in the above-identified patent and that said Letters Patent is hereby corrected as shown below:

Column 3, line 33, replace "Figure 2" with --Figures 2A and 2B--

Signed and Sealed this

Ninth Day of February, 1999

Attest:

Attesting Officer

*Acting Commissioner of Patents and Trademarks*